United States Patent
Sixl

(10) Patent No.: US 6,479,432 B1
(45) Date of Patent: Nov. 12, 2002

(54) NON-AQUEOUS OR LOW-WATER SUSPENSION CONCENTRATES OF MIXTURES OF ACTIVE COMPOUNDS FOR CROP PROTECTION

(75) Inventor: Frank Sixl, Selters-Haintchen (DE)

(73) Assignee: Aventis CropScience GmbH, Frankfurt (DE)

( * ) Notice: Subject to any disclaimer, the term of this patent is extended or adjusted under 35 U.S.C. 154(b) by 0 days.

(21) Appl. No.: 09/694,872

(22) Filed: Oct. 24, 2000

(30) Foreign Application Priority Data

Oct. 26, 1999 (DE) .......................... 199 51 427

(51) Int. Cl.[7] .................. A01N 25/22; A01N 39/02; A01N 43/54; A01N 43/66; A01N 47/36
(52) U.S. Cl. ................. 504/103; 504/106; 504/107; 504/135; 504/136
(58) Field of Search ................. 504/103, 106, 504/107, 135, 136

(56) References Cited

U.S. PATENT DOCUMENTS

| | | | |
|---|---|---|---|
| 5,518,991 A | 5/1996 | Frisch et al. | 504/138 |
| 5,573,998 A | 11/1996 | Frisch et al. | 504/211 |
| 5,707,926 A | 1/1998 | Frisch et al. | 504/116 |
| 5,990,047 A | 11/1999 | Hacker et al. | 504/134 |
| 6,096,687 A * | 8/2000 | Parrish | 504/130 |

FOREIGN PATENT DOCUMENTS

| | | |
|---|---|---|
| EP | 0 313 317 B1 | 4/1992 |
| EP | 0 554 015 | 8/1993 |
| WO | WO 00/25586 | 5/2000 |

* cited by examiner

*Primary Examiner*—S. Mark Clardy
(74) *Attorney, Agent, or Firm*—Frommer Lawrence & Haug LLP

(57) ABSTRACT

The invention relates to stable liquid and highly effective suspension concentrates comprising

- a) one or more solid herbicidally active compounds from the group of the sulfonylureas in suspended form,
- b) one or more active compounds which are partially or completely dissolved in component c),
- c) an organic solvent or solvent mixture,
- d) one or more nonionic emulsifiers,
- e) optionally one or more ionic emulsifiers,
- f) optionally one or more thickeners or thixotropic agents and no water or up to 30 percent by weight of water in dissolved form.

16 Claims, No Drawings

NON-AQUEOUS OR LOW-WATER SUSPENSION CONCENTRATES OF MIXTURES OF ACTIVE COMPOUNDS FOR CROP PROTECTION

The invention relates to storage-stable non-aqueous or low-water suspension concentrates in the form of suspensions which comprise at least one solid, specifically from the group of the herbicidal sulfonylureas, dispersed in the organic phase, and surfactants, and other active compounds dissolved in the organic phase.

Herbicidally active compounds from the group of the sulfonylureas, such as, for example, the 1-[(hetero)aryl(oxy)sulfonyl]-3-pyrimidin-2-yl- or 1-[(hetero)aryl(oxy)sulfonyl]-3-(1,3,5-triazin-2-yl)ureas, are predominantly formulated in the form of water-dispersible powders (WP) or water-dispersible granules (WG). One reason why solid formulations are preferred is in most cases the pronounced sensitivity to hydrolysis of the active compounds of this substance class. Since, at the same time, they are relatively soluble in water, the development of liquid water-based formulations is extremely difficult if the chemical stability of the sulfonylurea is to be ensured. Thus, in the literature, storage-stable aqueous suspension concentrates (SC) (see EP-0514768) and aqueous suspoemulsions (SE) (see EP-0514769) comprising sulfonylureas have been described only for a few special cases. On the other hand, water-free liquid formulations of active compounds or active compound mixtures with suspended solids are frequently physically unstable. On storage, dispersed solids tend to form deposits or agglomerates, to change the viscosity of and/or to cause inhomogeneities in the preparation.

The preparation of liquid formulations of herbicidal sulfonylureas is of particular interest when these active compounds are to be combined with liquid adjuvants and/or dissolved active compounds which are to improve the use properties, for example the herbicidal action. Suitable dissolved active compounds which are additionally present in the preparation are, for example, one or more herbicidally active substances and/or one or more safeners having one or both of the two properties below:

1. The active compound to be combined with the sulfonylurea is an organic compound with a low melting point which cannot be formulated easily as wettable powder (WP) or water-dispersible granules (WG) with satisfactory use properties.
2. It is a substance whose activity in the formulation is enhanced, optimized or reliably reproducible when it is dissolved in an emulsifiable organic solvent or when it is combined with certain liquid or dissolved auxiliaries, so-called adjuvants.

A commercially important group of active compounds having the above properties is that of the substituted phenoxypropionic acid derivatives, for example of the heteroaryloxyphenoxy- or the phenoxyphenoxypropionic acid derivatives. Thus, for example, it is known that the activity of fenoxaprop-P-ethyl against important weed grasses is improved when, on application, sufficiently high amounts of a nonionic wetting agent, for example a fatty alcohol polyglycol ether (for example ®Genapol X-060, Clariant), are dissolved in the spray liquor. Furthermore, for use in crops of cereals, fenoxaprop-P-ethyl is usually employed with the crop-plant-protecting substance (safener, antidote) mefenpyr-diethyl, which has a very low melting point of 52–54° C. Owing to the abovementioned physical properties of the components, it is easily understood that the commercial combinations of fenoxaprop-P-ethyl/mefenpyr-diethyl are formulated in liquid form, either as emulsions in water (EW) or as emulsifiable concentrate (EC). Accordingly, clodinafop-propargyl, which belongs to the same class of active compounds as fenoxaprop-P-ethyl and has a melting point of 48.2–57.1° C., likewise has physical properties which are unfavorable for solid formulations. Combinations of this herbicide with the safener cloquintocet-mexyl are currently commercially available exclusively in the form of emulsifiable concentrates.

Further suitable active compounds which can be employed partially or completely dissolved in an organic solvent are, for example, also herbicides from the group of the hydroxybenzonitriles, such as ioxynil and bromoxynil and their commercial salts and esters. Alternatively, the further active compound different from the sulfonylurea can be a safener, without a further herbicide being present, or an active compound mixture of a further herbicide and a safener is added, where the additional active compounds are preferably substantially dissolved in an organic solvent.

In contrast to the abovementioned active compounds in liquid formulation, herbicides from the group of the sulfonylureas are, as mentioned, for reasons of stability in most cases formulated as wettable powders (WP) or water-dispersible granules (WG). However, EP-0313317 also discloses non-aqueous suspension concentrates for certain pyridylsulfonylureas where the active compound is suspended in a vegetable oil to increase the herbicidal activity and selectivity of the sulfonylurea. EP-0313317 does not discuss the chemical stability of the sulfonylurea in the formulation. Furthermore, formulations of herbicide mixtures and details which would allow the chemical or physical stability of herbicide combinations to be estimated are missing. In principle, the amount of dissolved active compounds in the organic phase can affect the stability of the suspension of the sulfonylurea. It is also generally known that a combination of active compounds in a coformulation can reduce the chemical stability of the active compounds (so-called incompatibility of the active compounds) or else reduce their biological availability or, in general, activity.

With respect to the combinations of sulfonylureas with active compounds from other structure classes, which, in most cases, are not formulated or cannot be formulated as granules or wettable powders, it was therefore the object to provide a liquid formulation for sulfonylureas which, with respect to the physical stability of the formulation, the chemical stability of the sulfonylureas and, if possible, also the biological activity of the sulfonylureas, is an alternative to or an improvement of the WP and WG formulations. It was another object to provide a stable liquid formulation which is compatible with the use requirements and the physical properties of all active compounds contained therein.

Surprisingly, it has now been found that storage-stable liquid, low-water or water-free formulations of sulfonylureas and one or more other active compounds can be prepared by dispersing (=suspending) the solid sulfonylurea in a solvent/sufractant mixture which comprises, in dissolved form, at least one further active compound.

Accordingly, the invention provides liquid preparations (formulations) in the form of suspension concentrates, which comprise a) one or more solid herbicidally active compounds from the group of the sulfonylureas in suspended form,
b) one or more active compounds which are partially or completely dissolved in component c),
c) an organic solvent or solvent mixture,
d) one or more nonionic emulsifiers,
e) optionally one or more ionic emulsifiers,
f) optionally one or more thickeners or thixotropic agents and no water or up to 30 percent by weight of water in dissolved form.

The amount of sulfonylurea "in suspended form" means that the total amount of sulfonylurea or a part of the sulfonylurea is present undissolved in finely distributed form. Thus, it is also possible that part of the active compound is present in dissolved form. In the suspension concentrate, the sulfonylurea is preferably present substantially in undissolved form.

In addition, the suspension concentrates according to the invention may comprise the tackifiers, wetting agents, dispersants, penetrants, preservatives, antifreeze agents and solvents, fillers, carriers and colorants, antifoams, evaporation inhibitors and pH and viscosity regulators which are customary in each case. As long as they do not interfere; further emulsifiers, for example nonionic, anionic, cationic or amphoteric emulsifiers, may also be present, if appropriate.

Based on the formulations according to the invention, it is also possible to prepare, if appropriate, combinations with other pesticidally active compounds, such as, for example, insecticides, acaricides, herbicides, fungicides, and also with safeners, fertilizers and/or plant growth regulators.

Suitable active compounds for component b) are active compounds for crop protection compositions, for example herbicides, unless they are included in component a), or safeners, fungicides, insecticides, plant growth regulators and the like.

Preferably, the formulations comprise, as component b), safeners which, in combination with the herbicides a) that are present and any herbicidally active compounds b), reduce or prevent the phytotoxic effects of the herbicides on crop plants.

Preferably, the formulations also comprise, as component b), herbicidally active compounds from the group of the substituted phenoxypropionic acid derivatives.

To exclude hydrolytic decomposition of the sulfonylureas contained in the formulations, it is possible to prepare the formulations in water-free form. However, depending on the specific case, this may mean a considerable technical expense, in particular since many surfactants, owing to the way in which they are prepared, contain water. Surprisingly, however, it is not necessary to prepare the formulations in a completely water-free form. Within certain limits, the presence of water is indeed tolerated. Thus, it has been found that, in general, a water content of up to 2% by weight, in exceptional cases of up to 10% by weight, in the suspension concentrate does not adversely affect stability, or only to a small extent. Provided the water content does not lead to a w/o emulsion being formed, it is furthermore even feasible to add, in specific cases, water to the formulation, if this improves, for example, certain physical-chemical properties, for example the flowability of the product or the spontaneity with which the formulation is emulsified in water on dilution to give the spray liquor. The overall water content tolerated will depend strongly on the actual sensitivity to hydrolysis of the active compound, and on the solubility of the water in the solvent/surfactant mixture in question. In general, the water content of the product is in the range from 0 to 30% by weight, preferably from 0 to 20% by weight, in particular from 0 to 3% by weight, especially from 0 to 2% by weight, very particularly preferably from 0 to 1% by weight.

Suitable herbicides from the group of the sulfonylureas are, for example:
A) pyrimidinyl- or triazinylaminocarbonyl[benzene-, pyridine-, pyrazole-, thiophene- and (alkylsulfonyl) alkylamino-]sulfonamides and salts thereof. Preferred substituents on the pyrimidine ring or triazine ring are alkoxy, alkyl, haloalkoxy, haloalkyl, halogen or dimethylamino, where all substituents can be combined independently of one another. Preferred substituents in the benzene, pyrifine, pyrazole, thiophene or (alkylsulfonyl)alkylamino moiety are alkyl, alkoxy, halogen, nitro, alkoxycarbonyl, aminocarbonyl, alkylaminocarbonyl, dialkylaminocarbonyl, alkoxyaminocarbonyl, haloalkoxy, haloalkyl, alkylcarbonyl, alkoxyalkyl, (alkanesulfonyl)alkylamino. Suitable sulfonylureas are, for example, A1) phenyl- and benzylsulfonylureas and salts thereof and related compounds, for example
1-(2-chlorophenylsulfonyl)-3-(4-methoxy-6-methyl-1,3,5-triazin-2-yl)urea (chlorsulfuron),
1-(2-ethoxycarbonylphenylsulfonyl)-3-(4-chloro-6-methoxypyrimidin-2-yl)urea (chlorimuron-ethyl),
1-(2-methoxycarbonylphenylsulfonyl)-3-(4-methoxy-6-methyl-1,3,5-triazin-2-yl)urea (metsulfuron-methyl),
1-(2-chloroethoxyphenylsulfonyl)-3-(4-methoxy-6-methyl-1,3,5-triazin-2-yl)urea (triasulfuron),
1-(2-(2-methoxyethoxy)phenylsulfonyl)-3-(4,6-dimethoxy-1,3,5-triazin-2-yl)urea (cinosulfuron),
1-(2-(3,3,3-trifluoropropyl)phenylsulfonyl)-3-(4-methoxy-6-methyl-1,3,5-triazin-2-yl)urea (prosulfuron),
1-(2-methoxycarbonylphenylsulfonyl)-3-(4-ethoxy-6-methylamino-1,3,5-triazin-2-yl)urea (ethametsulfuron-methyl),
1-(2-methoxycarbonylphenylsulfonyl)-3-(4,6-dimethylpyrimidin-2-yl)urea (sulfometuron-methyl),
1-(2-methoxycarbonylphenylsulfonyl)-3-(4-methoxy-6-methyl-1,3,5-triazin-2-yl)-3-methylurea (tribenuron-methyl),
1-(2-methoxycarbonylbenzylsulfonyl)-3-(4,6-dimethoxypyrimidin-2-yl)urea (bensulfuron-methyl),
1-(2-methoxycarbonylphenylsulfonyl)-3-(4,6-bis(difluoromethoxy)pyrimidin-2-yl)urea (primisulfuron-methyl),
3-(4-ethyl-6-methoxy-1,3,5-triazin-2-yl)-1-(2,3-dihydro-1,1-dioxo-2-methylbenzo[b]thiophene-7-sulfonyl)urea (see EP-A-79683),
3-(4-ethoxy-6-ethyl-1,3,5-triazin-2-yl)-1-(2,3-dihydro-1,1-dioxo-2-methylbenzo[b]thiophene-7-sulfonyl)urea (see EP-A-79683),
3-(4-methoxy-6-methyl-1,3,5-triazin-2-yl)-1-(2-methoxycarbonyl-5-iodophenylsulfonyl)urea or its sodium salt (iodosulfuron-methyl or its sodium salt, see WO 92/13845) or the parent acid iodosulfuron or salts thereof,
DPX-66037, triflusulfuron-methyl (see Brighton Crop Prot. Conf.—Weeds—1995, p. 853),
CGA-277476, (oxasulfuron, see Brighton Crop Prot. Conf.—Weeds—1995, p. 79),
methyl 2-[3-(4,6dimethoxypyrimidin-2-yl)ureidosulfonyl] 4-methylsulfonylamidomethylbenzoate (see WO 95/10507),
N,N-dimethyl-2-[3-(4,6-dimethoxypyrimidin-2-yl) ureidosulfonyl]-4-formylaminobenzamide (see PCT/EP 95/01344),
A2) thienylsulfonylureas and salts thereof, for example
1-(2-methoxycarbonylthiophen-3-ylsulfonyl)-3-(4-methoxy-6-methyl-1,3,5-triazin-2-yl)urea (thifensulfuron-methyl),
A3) pyrazolylsulfonylureas and salts thereof, for example
1-(4-ethoxycarbonyl-1-methylpyrazol-5-ylsulfonyl)-3-(4,6-dimethoxypyrimidin-2-yl)urea (pyrazosulfuron-ethyl),
methyl 3-chloro-5-(4,6-dimethoxypyrimidin-2-ylcarbamoylsulfamoyl)-1-methylpyrazole-4-carboxylate (halosulfuron-methyl, see EP 282613),
methyl 5-(4,6-dimethylpyrimidin-2-yl-carbamoylsulfamoyl)-1-(2-pyridyl)pyrazole-4-carboxylate (NC-330, see Brighton Crop Prot. Conference—Weeds—1991, Vol.1, p. 45 ff.),
DPX-A8947, azimsulfuron, (see Brighton Crop Prot. Conf.—Weeds—1995, p. 65), A4) sulfondiamide derivatives and salts thereof, for example 3-(4,6-dimethoxypyrimidin-2-yl)-1-(N-methyl-N-methylsulfonylaminosulfonyl)urea (amidosulfuron) and structural analogs (see EP-A-131258 and Z. Pfl. Krankh. Pfl. Schutz, Special issue XII, 489–497 (1990));

cyclosulfamuron, that is to say 1-[2-(cyclopropylcarbonyl) phenylsulfamoyl]-3-(4,6-dimethoxypyrimidin-2-yl)urea (EP 463287);

A5) pyridylsulfonylureas and salts thereof, for example
1-(3-(N,N-dimethylaminocarbonyl)pyridin-2-ylsulfonyl)-3-(4,6-dimethoxypyrimidin-2-yl)urea (nicosulfuron),
1-(3-ethylsulfonylpyridin-2-ylsulfonyl)-3-(4,6-dimethoxypyrimidin-2-yl)urea (rimsulfuron),
1-(3-trifluoromethylpyridin-2-ylsulfonyl)-3-(4,6-dimethoxypyrimidin-2-yl)urea (flazasulfuron),
methyl 2-[3-(4,6-dimethoxypyrimidin-2-yl)ureidosulfonyl]-6-trifluoromethyl-3-pyridinecarboxylate, sodium salt (DPX-KE459, flupyrsulfuron, see Brighton Crop Prot. Conf.—Weeds—1995, p. 49).

Pyridylsulfonylureas and salts thereof, as described in DE-A4000503 and DE-A-4030577, are preferably those of the formula
in which
E is CH or N, preferably CH,
$R^6$ is iodine or $NR^{11}R^{12}$,
$R^7$ is H, halogen, cyano, $(C_1-C_3)$-alkyl, $(C_1-C_3)$-alkoxy, $(C_1-C_3)$-haloalkyl, $(C_1-C_3)$-haloalkoxy, $(C_1-C_3)$-alkylthio, $(C_1-C_3)$-alkoxy-$(C_1-C_3)$-alkyl, $(C_1-C_3)$-alkoxy-carbonyl, mono- or di-$((C_1-C_3)$-alkyl)-amino, $(C_1-C_3)$-alkylsulfinyl or -sulfonyl, $SO_2-NR^aR^b$ or $CO-NR^aR^b$, in particular H,
$R^a$, $R^b$ independently of one another are H, $(C_1-C_3)$-alkyl, $(C_1-C_3)$-alkenyl, $(C_1-C_3)$-alkynyl or together are $-(CH_2)_4-$, $-(CH_2)_5-$ or $(CH_2)_2-O-(CH_2)_2-$,
$R^8$ is H or $CH_3$,
$R^9$ is halogen, $(C_1-C_2)$-alkyl, $(C_1-C_2)$-alkoxy, $(C_1-C_2)$-haloalkyl, preferably $CF_3$, $(C_1-C_2)$-haloalkoxy, preferably $OCHF_2$ or $OCH_2CF_3$,
$R^{10}$ is $(C_1-C_2)$-alkyl, $(C_1-C_2)$-haloalkoxy, preferably $OCHF_2$, or $(C_1-C_2)$-alkoxy, and
$R^{11}$ is $(C_1-C_4)$-alkyl and
$R^{12}$ is $(C_1-C_4)$-alkylsulfonyl or
$R^{11}$ and $R^{12}$ together are a chain of the formula $-(CH_2)_3SO_2-$ or $-(CH_2)_4SO_2-$,
for example 3-(4,6-dimethoxypyrimidin-2-yl)-1-($^3$-N-methylsulfonyl-N-laminopyridin-2-yl)sulfonylurea, or salts thereof, A6) alkoxyphenoxysulfonylureas and salts thereof, as described in EP-A-0342569, preferably 3-(4,6-dimethoxypyrimidin-2-yl)-1-(2-ethoxyphenoxy) sulfonylurea, or salts thereof (ethoxysulfuron), A7) imidazolylsulfonylureas and salts thereof, for example MON37500, sulfosulfuron (see Brighton Crop Prot. Conf.—Weeds—1995, p.57); TH-913, imazosulfuron and other related sulfonylurea derivatives and mixtures thereof.

By exchanging a hydrogen atom (more accurately a proton) of their amide group —$SO_2NH$— or, if appropriate, of other groups having acidic hydrogen atoms, for example carboxyl groups, for an agriculturally suitable cation, the sulfonylureas can form salts. These salts are, for example, metal salts, preferably alkali metal or alkaline earth metal salts, in particular sodium and potassium salts, or ammonium salts, or else ammonium salts which are substituted by one to four organic radicals. The sulfonylurea compounds are also capable of forming salts by adding a suitable inorganic or organic acid, such as, for example, HCl, HBr, $H_2SO_4$ or $HNO_3$, but also oxalic acid or sulfonic acids, to a basic group, such as, for example, amino or alkylamino. Suitable substituents, such as, for example, sulfonic acid or carboxylic acid groups can also form inner salts with groups which for their part can be protonated, such as amino groups. The salts are embraced by the sulfonylureas which can be used according to the invention, unless indicated otherwise, and can be used analogously.

Preference is given to the sulfonylureas chlorsulfuron, chlorimuron-ethyl, metsulfuron-methyl, triasulfuron, cinosulfuron, prosulfuron, ethametsulfuron-methyl, sulfometuron-methyl, tribenuron-methyl, bensulfuron-methyl, primisulfuron-methyl, iodosulfuron-methyl, triflusulfuron-methyl, oxasulfuron, methyl 2-[3-(4,6-dimethoxypyrimidin-2-yl)ureidosulfonyl]-4-methylsulfonylamidomethylbenzoate, N,N-dimethyl-2-[3-(4,6-dimethoxypyrimidin-2-yl)ureidosulfonyl]-4-formylaminobenzamide, thifensulfuron-methyl, amidosulfuron, ethoxysulfuron and salts thereof, in particular chlorsulfuron, chlorimuron-ethyl, metsulfuron-methyl, triasulfuron, cinosulfuron, prosulfuron, ethametsulfuron-methyl, sulfometuron-methyl, tribenuron-methyl, bensulfuron-methyl, primisulfuron-methyl, iodosulfuron-methyl-sodium, triflusulfuron-methyl, methyl 2-[3-(4,6-dimethoxypyrimidin-2-yl)ureidosulfonyl]4-methylsulfonylamidomethylbenzoate, N,N-dimethyl-2-[3-(4,6-dimethoxypyrimidin-2-yl)ureidosulfonyl]4-formylaminobenzamide, thifensulfuron-methyl, amidosulfuron, ethoxysulfuron and salts thereof.

The formulations according to the invention comprise herbicidally active compounds from the group of the sulfonylureas in amounts of, for example, from 0.1 to 50% by weight, preferably from 0.1 to 20% by weight, in particular from 0.2 to 5% by weight, based on the weight of the formulation.

Suitable herbicides of the type of the substituted phenoxypropionic acid derivatives (for component b) are, for example B1) phenoxyphenoxy- and benzyloxyphenoxycarboxylic acid derivatives, for example
methyl 2-(4-(2,4-dichlorophenoxy)phenoxy)propionate (diclofop-methyl),
methyl 2-(4-(4-bromo-2-chlorophenoxy)phenoxy) propionate (see DE-A-2601548),
methyl 2-(4-(4-bromo-2-fluorophenoxy)phenoxy) propionate (see U.S. Pat. No. 4,808,750),
methyl 2-(4-(2-chloro-4-trifluoromethylphenoxy)phenoxy) propionate (see DE-A-2433067),
methyl 2-(4-(2-fluoro-4-trifluoromethylphenoxy)phenoxy) propionate (see U.S. Pat. No. 4,808,750),
methyl 2-(4-(2,4-dichlorobenzyl)phenoxy)propionate (see DE-A-2417487),
ethyl 4-(4-(4-trifluoromethylphenoxy)phenoxy)pent-2-enoate,
methyl 2-(4-(4-trifluoromethylphenoxy)phenoxy) propionate (see DE-A-2433067),
butyl 2-(4-(4-cyano-2-fluorophenoxy)phenoxy)propionate (cyhalofop-butyl, DEH-112)

B2) "monocyclic" heteroaryloxyphenoxyalkanecarboxylic acid derivatives, for example
ethyl 2-(4-(3,5-dichloropyridyl-2-oxy)phenoxy)propionate (see EP-A-2925),
propargyl 2-(4-(3,5-dichloropyridyl-2-oxy)phenoxy) propionate (EP-A-3114),
butyl 2-(4-(3,5-dichloropyridyl-2-oxy)phenoxy)propionate (pirifenop-butyl),
methyl 2-(4-(3-chloro-5-trifluoromethyl-2-pyridyloxy) phenoxy)propionate (haloxyfop-methyl, see EP-A-3890)

and other esters and the corresponding active compounds from the D series (haloxyfop-P), ethyl 2-(4-(3-chloro-5-trifluoromethyl-2-pyridyloxy) phenoxy)propionate (see EP-A-3890), propargyl (2R)-2-(4-(5-chloro-3-fluoro-2-pyridyloxy) phenoxy)propionate (clodinafop-propargyl, see EP-A-191736), butyl 2-(4-(5-trifluoromethyl-2-pyridyloxy)phenoxy) propionate (fluazifop-butyl) and other esters and the corresponding active compounds from the series (fluazifop-P), isoxapyrifop (HOK-868)

B3) "bicyclic" heteroaryloxyphenoxyalkanecarboxylic acid derivatives, for example methyl, ethyl and tetrahydrofuran-2-ylmethyl 2-(4-(6-chloro-2-quinoxalyloxy)phenoxy)propionate (quizalofop-methyl, -ethyl and -tefuryl) and the corresponding active compounds from the D series (quizalofop-P), methyl 2-(4-(6-fluoro-2-quinoxalyloxy)phenoxy)propionate (see J. Pest. Sci. Vol. 10, 61 (1985)), 2R-2-(4-(6-chloro-2-quinoxalyloxy)phenoxy)propionic acid and its 2-isopropylideneaminooxyethyl ester (propaquizafop), ethyl 2-(4-(6-chlorobenzoxazol-2-yloxy)phenoxy) propionate (fenoxaprop-ethyl), its D(+) isomer (fenoxaprop-P-ethyl) and ethyl 2-(4-(6-chlorobenzothiazol-2-yloxy)phenoxy) propionate (see DE-A-2640730).

Preferred suitable phenoxypropionic acid derivatives are: diclofop-methyl, cyhalofop-butyl, pirifenop-butyl, haloxyfop-methyl, haloxyfop-P-methyl, clodinafop-propargyl, fluazifop-butyl, fluazifop-P-butyl, quizalofop-methyl or -ethyl or -tefuryl, quizalofop-P-methyl or -ethyl or -tefuryl, propaquizafop, fenoxaprop-ethyl, fenoxaprop-P-ethyl.

Particularly suitable are fenoxaprop-ethyl, fenoxaprop-P-ethyl, clodinafop-propargyl and cyhalofop-butyl.

If the formulations according to the invention comprise herbicidally active compounds from the group of the phenoxypropionic acid derivatives, they comprise the phenoxypropionic acid (derivative) advantageously in amounts of, for example, from 0.5 to 50% by weight, preferably from 2 to 30% by weight, in particular from 5 to 15% by weight, based on the weight of the formulation.

Preferred components b) in the formulations are also safeners which are advantageous and generally matched, in a manner known to the person skilled in the art, to individual or more than one of the active compounds contained in the formulation. In general, the following active compounds are suitable for use as safeners:

(a) Compounds of the type of the dichlorophenylpyrazoline-3-carboxylic acid, preferably compounds such as ethyl 1-(2,4-dichlorophenyl)-5-(ethoxycarbonyl)-5-methyl-2-pyrazoline-3-carboxylate (S1-1) ("mefenpyr-diethyl", PM, pp. 781–782), and related compounds, as described in WO 91/07874.

(b) Derivatives of dichlorophenylpyrazole carboxylic acid, preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)5-(1,1-dimethylethyl)pyrazole-3-carboxylate (S1-4), ethyl 1-(2, 4-dichlorophenyl)-5-phenylpyrazole-3-carboxylate (S1-5) and related compounds as described in EP-A-333 131 and EP-A-269 806.

(c) Compounds of the type of the triazolecarboxylic acids, preferably compounds such as fenchlorazole(ethyl ester), that is to say ethyl 1-(2,4-dichlorophenyl)-5-trichloromethyl-(1H)-1,2,4-triazole-3-carboxylate (S1-6) and related compounds EP-A-174 562 and EP-A-346 620.

(d) Compounds of the type of the 5-benzyl- or 5-phenyl-2-isoxazoline-3-carboxylic acid, or the 5,5-diphenyl-2-isoxazoline-3-carboxylic acid, preferably compounds such as ethyl 5-(2,4-dichlorobenzyl)-2-isoxazoline-3-carboxylate (S1-7) or ethyl 5-phenyl-2-isoxazoline-3-carboxylate (S1-8) and related compounds, as described in WO 91/08202, or ethyl 5,5-diphenyl-2-isoxazolinecarboxylate (S1-9) ("isoxadifen-ethyl") or its -n-propyl ester (S1-10) or ethyl 5-(4-fluorophenyl)-5-phenyl-2-isoxazoline-3-carboxylate (S1-11), as described in the German patent application (WO-A-95/07897).

(e) Compounds of the type of the 8-quinolineoxyacetic acid (S2), preferably 1-methylhex-1-yl (5-chloro-8-quinolineoxy) acetate (common name "cloquintocet-mexyl" (S2-1) (see PM, pp. 263–264) 1,3-dimethylbut-1-yl (5-chloro-8-quinolineoxy)acetate (S2-2), 4-allyloxybutyl (5-chloro-8-quinolineoxy)acetate (S2-3), 1-allyloxyprop-2-yl (5-chloro-8-quinolineoxy)acetate (S2-4), ethyl (5-chloro-8-quinolineoxy)acetate (S2-5), methyl (5-chloro-8-quinolineoxy)acetate (S2-6), allyl (5-chloro-8-quinolineoxy)acetate (S2-7), 2-(2-propylideneiminoxy)-1-ethyl (5-chloro-8-quinolineoxy)acetate (S2-8), 2-oxoprop-1-yl (5-chloro-8-quinolineoxy)acetate (S2-9) and related compounds, as described in EP-A-86 750, EP-A-94 349 and EP-A-191 736 or EP-A-0 492 366.

(f) Compounds of the type of the (5-chloro-8-quinolineoxy) malonic acid, preferably compounds such as diethyl (5-chloro-8-quinolineoxy)malonate, diallyl (5-chloro-8-quinolineoxy)malonate, methyl ethyl (5-chloro-8-quinolineoxy)malonate and related compounds, as described in EP-A-0 582 198.

(g) Active compounds of the type of the phenoxyacetic or -propionic acid derivatives or the aromatic carboxylic acids, such as, for example, 2,4-dichlorophenoxyacetic acid (esters) (2,4-D), 4-chloro-2-methylphenoxypropionic esters (mecoprop), MCPA or 3,6-dichloro-2-methoxybenzoic acid (esters) (dicamba).

(h) Active compounds of the type of the pyrimidines, which are used as soil-acting safeners in rice, such as, for example, "fenclorim" (PM, pp. 511–512) (=4,6-dichloro-2-phenylpyrimidine), which is known as safener for pretilachlor in sown rice.

(i) Active compounds of the type of the dichloroacetamides, which are frequently used as pre-emergent safeners (soil-acting safeners), such as, for example, "dichlormid" (PM, pp. 363-364) (=N,N-diallyl-2,2-dichloroacetamide), "R-29148" (=3-dichloroacetyl-2,2,5-trimethyl-1,3-oxazolidine from Stauffer), "benoxacor" (PM, pp. 102–103) (=4-dichloroacetyl-3,4-dihydro-3-methyl-2H-1,4-benzoxazine), "PPG-1292" (=N-allyl-N-[(1,3-dioxolan-2-yl)methyl] dichloroacetamide from PPG Industries), "DK-24" (=N-allyl-N-[(allylaminocarbonyl)methyl] dichloroacetamide from Sagro-Chem), "AD-67" or "MON 4660" (=3-dichloroacetyl-1-oxa-3-aza-spiro[4,5]decane from Nitrokemia or Monsanto), "diclonon" or "BAS145138" or "LAB145138" (=3-dichloroacetyl-2,5,5-trimethyl-1,3-diazabicyclo[4.3.0]nonane from BASF) and "furilazol" or "MON 13900" (see PM, 637–638) (=(RS)-3-dichloroacetyl-5-(2-furyl)-2,2-dimethyloxazolidine).

(k) Active compounds of the type of the dichloroacetone derivatives, such as, for example, "MG 191" (CAS-Reg. No. 96420-72-3) (=2-dichloromethyl-2-methyl-1,3-dioxolane from Nitrokemia), which is known as safener for maize.

(l) Active compounds of the type of the oxyimino compounds, which are known as seed dressings, such as, for example, "oxabetrinil" (PM, pp. 902–903) (=(Z)-1,3-dioxolan-2-ylmethoxyimino(phenyl)acetonitrile), which is known as seed dressing safener for millet against metolachlor damage.

"fluxofenim" (PM, pp. 613–614) (=1-(4-chlorophenyl)-2,2,2-trifluoro-1-ethanone O-(1,3-dioxolan-2-ylmethyl) oxime), which is known as seed dressing safener for millet against metolachlor damage, and "cyometrinil" or "-CGA43089" (PM, p. 1304) (=(Z)-Cyanomethoxyimino(phenyl)acetonitrile), which is known as seed dressing safener for millet against metolachlor damage.

(m) Active compounds of the type of the thiazolecarboxylic esters, which are known as seed dressings, such as, for example, "flurazol" (PM, pp. 590–591) (=benzyl 2-chloro-4-trifluoromethyl-1,3-thiazole-5-carboxylate), which is known as seed dressing safener for millet against alachlor and metolachlor damage.

(n) Active compounds of the type of the naphthalenedicarboxylic acid derivatives, whch are known as seed dressings, such as, for example, "naphthalic anhydride" (PM, p.1342) (=1,8-naphthalenedicarboxylic anhydride), which is known as seed dressing safener for maize against thiocarbamate herbicide damage.

(o) Active compounds of the type of the chromaneacetic acid derivatives, such as, for example, "CL 304415" (CAS-Reg. No. 31541-57-8) (=2-(4-carboxychroman-4-yl)acetic acid from American Cyanamid), which is known as safener for maize against imidazolinone damage.

(p) Active compounds which, in addition to a herbicidal action against harmful plants, also have safener action in crop plants such as rice, such as, for example, "dimepiperate" or "MY-93" (PM, pp.404–405) (=S-1-methyl-1-phenylethyl piperidine-1-thiocarboxylate), which is known as safener for rice against damage by the herbicide molinate, "daimuron" or "SK 23" (PM, p. 330) (=1-(1-methyl-1-phenylethyl)-3-p-tolylurea), which is known as safener for rice against damage by the herbicide imazosulfuron, "cumyluron"="JC-940" (=3-(2-chlorophenylmethyl-1-(1-methyl-1-phenylethyl)urea, see JP-A-60087254), which is known as safener for rice against damage by some herbicides, "methoxyphenon" or "NK 049" (=3,3'-dimethyl-4-methoxy-benzophenone), which is known as safener for rice against damage by some herbicides, "CSB" (=1-bromo4-(chloromethylsulfonyl)benzene) (CAS-Reg. No. 54091-064 from Kumiai), which is known as safener against damage by some herbicides in rice.

(q) N-Acylsulfonamides of the formula (S3) and salts thereof
as described in WO-A-97/45016.

(r) Acylsulfamoylbenzamides of the formula (S4), if appropriate also in salt form,
as described in the International Application No. PCT/EP98/06097, and (s) Compounds of the formula (S5),
as described in WO-A 98/13 361, including the stereoisomers and the salts used in agriculture.

Of particular interest among the safeners mentioned are mefenpyr-diethyl (S1-1), isoxadifen-ethyl (S1-9) and cloquintocet-mexyl (S2-1), in particular (S1-1) or (S1-9) in formulations with a sulfonylurea as herbicidally active compound, even as only active compound, or in particular also (S1-1) or (S1-9) in formulations comprising a sulfonylurea and, as further herbicidally active compound, fenoxaprop-ethyl or fenoxaprop-P-ethyl, and in particular also (S2-1) in formulations comprising a sulfonylurea and, as further herbicidally active compound, clodinafop-propargyl.

Unless mentioned with specific literature references, the active compounds mentioned are generally described in "The Pesticide Manual", 11th Edition, The British Crop Protection Council and the Royal Soc. of Chemistry, 1997, and the literature cited therein.

The weight ratio of herbicide components a) or, if appropriate, herbicide components a) and b) to safeners under the component b) can vary within a wide range, for example in the range of from 1:200 to 200:1, preferably from 1:100 to 100:1, in particular from 1:20 to 20:1, very particularly from 1:10 to 10:1.

The formulations according to the invention preferably comprise safeners in amounts of from 0.1 to 40% by weight, in particular from 0.1 to 15% by weight, very particularly from 1 to 5% by weight, based on the weight of the formulation.

The formulation according to the invention comprises the active compound component b) or mixtures of active compounds b) generally in amounts of from 0.1 to 60% by weight, preferably from 0.1 to 50% by weight, in particular from 0.5 to 30% by weight, very particularly from 3 to 20% by weight.

The amount of components a) and b) and, if appropriate, additional combination active compounds (total amount of active compound) is preferably in the range from 0.1 to 60% by weight, preferably from 0.6 to 50% by weight, in particular from 2.5 to 25% by weight, very particularly from 7 to 20% by weight.

Suitable organic solvents (component c) are, for example:
1. substantially nonpolar solvents, such as
   aromatic hydrocarbons derived from benzene, such as, for example, toluene, xylenes, mesitylene, diisopropylbenzene and its higher homologs, indane and naphthalene derivatives, such as 1-methyinaphthalene, 2-methyinaphthalene;
   aliphatic hydrocarbons, such as, for example, pentane, hexane, octane, cyclohexane, corresponding mineral oils from the aliphatic or isoparaffinic series, such as solvents from the ®Exol D series and the ®Isopor series from Exxon,
   mixtures of aromatic and aliphatic hydrocarbons, such as, for example, the corresponding "aromatic" mineral oils, such as mineral oils from the ®Solvesso series (Exxon),
   halogenated aliphatic hydrocarbons, such as methylene chloride,
   halogenated aromatic hydrocarbons, such as chlorobenzene, dichlorobenzenes;

2. polar lipophilic solvents, such as
   oils, for example oils of vegetable or animal origin, such as mixed or uniform fatty acid glycerol esters (in most cases triglycerides) or fatty acid glycol esters, in each case preferably based on saturated and/or unsaturated fatty acids having 8 to 24 carbon atoms, in particular 12 to 22 carbon atoms, for example corn germ oil, rapeseed oil, sunflower oil, cotton seed oil, linseed oil, soya oil, coconut oil, palm oil, thistle oil and castor oil,
   esters from the group of the saturated or unsaturated aliphatic carboxylic esters (monocarboxylic acid monoesters), preferably esters of aliphatic carboxylic acids having 1 to 24 carbon atoms and alkanols having 1 to 22 carbon atoms, in particular
   a) ($C_1$–$C_6$)-alkyl ($C_1$–$C_7$)-alkanecarboxylates, such as ethyl acetate,
   b) oil-like saturated or unsaturated ($C_8$–$C_{22}$)-fatty acid ($C_1$–$C_6$)-alkyl esters, such as alkyl caprylate, alkyl caprate, alkyl laurate, alkyl palmitate, alkyl stearate, alkyl oleate, alkyl linolate, alkyl linolenate, preferably having in each case 1 to 8 carbon atoms in the alcohol moiety, and derivatives of vegetable and animal oils, such as rapeseed oil fatty acid ($C_1$–$C_8$)-alkyl ester, preferably rapeseed oil fatty acid methyl ester (="rapeseed oil methyl ester") and rapeseed oil fatty acid ethyl ester (="rapeseed oil ethyl ester"),
   esters of aromatic carboxylic acids, such as phthalic acid ($C_1$–$C_{12}$)-alkyl esters, specifically phthalic ($C_4$–$C_8$)-alkyl esters, or esters of other organic acids,
   esters of other organic acids, such as alkylphosphonic acid esters, for example [($C_1$–$C_{18}$)-alkyl]phosphonic acid di[($C_1$–$C_{12}$)-alkyl) and/or cycloalkyl] esters, preferably a [($C_4$–$C_{16}$)-alkyl]phosphonic acid di[($C_1$–$C_{12}$)-alkyl]ester, in particular bis(2-ethylhexyl) octanephosphonate (Hoe S 4326, Clariant).
3. Mixtures of the solvents mentioned under 1 and/or 2,
4. Mixtures of one or more of the solvents mentioned under 1 and 2 and a minor fraction, that is to say less than 50% by weight, preferably less than 30% by weight, in particular less than 15% by weight, of a polar aprotic or protic solvent, such as
   ethers, such as tetrahydrofuran (THF), dioxane, alkylene glycol monoalkyl ethers and dialkyl ethers, such as, for example, propylene glycol monomethyl ether, propylene glycol monoethyl ether, ethylene glycol monomethyl ether or ethylene glycol monoethyl ether, diglyme and tetraglyme;
   amides, such as dimethylformamide (DMF), dimethylacetamide and N-alkylpyrrolidones, for example N-methylpyrrolidone (NMP);
   ketones, such as acetone;
   nitrites, such as acetonitrile, propionitrile, butyronitrile and benzonitrile;
   sulfoxides and sulfones, such as dimethyl sulfoxide (DMSO) and sulfolane;
   mono- or polyhydric alcohols having preferably 1 to 12 carbon atoms, such as methanol, ethanol, propanol, isopropanol, n-, iso-, sec- and tert-butanol, n-hexanol, n-octanol, n-decanol, n-dodecanol, ethylene glycol and glycerol.

When selecting or admixing polar solvents, preference is given to those solvents in which or in the mixture of which with the other organic solvents the sulfonylurea dissolves only sparingly.

Preferred solvents are:
aromatic solvents derived from benzene, such as xylene, mesitylene, indane, diisopropylbenzene and higher homologs and 6–16C-aromatics mixtures from the ®Solvesso series from Exxon, such as Solvesso® 100 (b.p. 162–177° C.), Solvesso® 150 (b.p. 187–207° C.) and Solvesso® 200 (b.p. 219–282° C.), or mixtures of the solvents mentioned;
nonaromatic solvents, for example the aliphatic and isoparaffinic solvents from the ®Exsol D and ®Isopor series from Exxon, in a mixture with an aromatic solvent;
oils of vegetable origin, such as fatty acid glycerol esters having 8 to 22 carbon atoms, preferably 12 to 22, in particular 18 carbon atoms, in the fatty acid moiety, for example rapeseed oil,
($C_8$–$C_{22}$) fatty acid ($C_1$–$C_6$)-alkyl esters, such as alkyl caprylate, alkyl caprate, alkyl laurate, alkyl palmitate, alkyl stearate, alkyl oleate, alkyl linolate, alkyl linolenate and rapeseed oil fatty acid ($C_1$–$C_6$)-alkyl esters, preferably rapeseed oil fatty acid methyl ester (="rapeseed oil methyl ester") and rapeseed oil fatty acid ethyl ester (="rapeseed oil ethyl ester"), in particular in a mixture with an aromatic solvent.

Particularly preferred solvents are:
aromatic solvents derived from benzene, such as xylene, mesitylene, indane, diisopropylbenzene,
aromatic solvents of 6–16C-aromatics mixtures, for example products from the ®Solvesso series from Exxon, such as, for example, Solvesso® 100 (b.p. 162–177° C.), Solvesso® 150 (b.p. 187–207° C.) and Solvesso® (b.p. 219–282° C.), or mixtures of the solvents mentioned,
mixtures of nonaromatic solvents and aromatic solvents, for example mixtures of aliphatic and isoparaffinic solvents from the ®Exsol D and ®Isopor series from Exxon and aromatic solvents such as the aromatic solvents mentioned above based on benzene or aromatics mixtures such as products from the ®Solvesso series;
($C_8$–$C_{22}$)-fatty acid ($C_1$–$C_4$)-alkyl esters, such as alkyl caprylate, alkyl caprate, alkyl laurate, alkyl palmitate, alkyl stearate, alkyl oleate, alkyl linolate, alkyl linolenate and rapeseed oil fatty acid ($C_1$–$C_4$)-alkyl esters, preferably rapeseed oil fatty acid methyl ester (="rapeseed oil methyl ester") and rapeseed oil fatty acid ethyl ester (="rapeseed oil ethyl ester"), in particular also those in a mixture with one of the aromatic solvents mentioned.

The total solvent content is, for example, in the range from 5 to 95% by weight, preferably from 10 to 90% by weight, in particular from 40 to 80% by weight, based on the weight of the formulation.

Suitable emulsifiers (component d) are, on their own or in combination with one another, in particular surfactants which are soluble in the solvent in question.

Nonionic surfactants which can be used according to the invention are, for example, the following:
ethoxylated, saturated and unsaturated aliphatic alcohols, preferably ethoxylated fatty alcohols having 8 to 24 carbon atoms in the alkyl radical and 1 to 100, in particular 2 to 50, ethyleneoxy units (EO) in the polyglycol moiety, for example ethoxylated isotridecyl alcohol, coconut fatty alcohol, oleyl alcohol, stearyl alcohol, tallow fatty alcohol, preferably ethoxylated isotridecyl or oleyl alcohol having a degree of ethoxylation of from 2 to 20, preferably from 3 to 8, EO, for example surfactants from the ®Genapol-X or Genapol-O series from Clariant, terminally etherified ethoxylated, saturated and unsaturated aliphatic alcohols, preferably ethoxylated fatty alcohols having 8 to 24 carbon atoms in the alkyl radical and 1 to 100, in particular 2 to 50, ethyleneoxy units (EO) in the polyethylene glycol moiety which are preferably terminally etherified with ($C_1$–$C_6$)-alkyl, in particular with methyl, ethyl, n- and i-propyl, n-, i-, sec- and tert-butyl, for example ethoxylated isotridecyl or oleyl alcohols having a degree of ethoxylation of from 2 to 20, preferably from 3 to 8, EO which are terminally etherified with methyl, ethyl, n- and i-propyl, n-, i-, sec- and t-butyl, for example surfactants from the ®Genapol-X alkyl ether or Genapol-O alkyl ether series from Clariant, preferably Genapol-X 060 methyl ether, ethoxylated arylalkylphenols, preferably tristyrylphenols having a mean EO chain length in the range from 10 to 80 EO, preferably from 16 to 40 EO, such as, for example, the products ®Soprophor BSU, Soprophor CY/8, Soprophor S/25 or Soprophor S/40-P available from Rhodia, ethoxylated alkylphenols having one or more alkyl radicals, for example having 1 to 12 C atoms, preferably nonylphenols, for example from the ®Arkopal-N series from Clariant having a degree of ethoxylation of from 2 to 40 EO, preferably from 4 to 15 EO, ethoxylated hydroxyfatty acids, preferably castor oil derivatives having a degree of ethoxylation of from 10 to 80 EO, preferably from 30 to 40 EO, such as, for example, ®Emulsogen EL and Emulsogen EL 400 from Clariant, surfactants from the group of the ethoxylated sorbitan esters, for example ®Atplus 309 F (ICI), block copolymers of ethylene oxide (EO) and propylene oxide (PO) of different chain lengths, for example having a molecular weight of the polypropylene oxide unit of from 200 to 10,000, preferably from 1000 to 4000, where the proportion of polyethylene glycol is preferably from 10 to 80 percent by weight, for example nonionic surfactants from the series ®Pluronic (BASF), such as Pluronic L and Pluronic PE, or ®Synperonic (Uniqema), such as Synperonic PE P 75 and Synperonic PE L 121, condensates of EO/PO block copolymers and ethylenediamine, for example having a molecular weight of the polypropylene oxide unit of from 200 to 10,000, preferably from 2000 to 6000, where the proportion of polyethylene glycol is preferably from 10 to 80 percent by weight, for example nonionic surfactants from the series ®Pluronic T (BASF) or ®Synperonic T (Uniqema), such as ®Synperonic T 707 or ®Synperonic T 908.

Depending on the type of emulsifier used, the chemical stability of the sulfonylurea(s) contained in the formulation can vary. It is frequently observed that the stability is increased if surfactants having a blocked hydroxy function are used. This fact is supported by the working examples (see further below). Thus, in the formulations which, for example, comprise the methyl ether of ®Genapol X-060 (see Table 1, Examples 7 and 8), little (<5%) if any chemical decomposition of the sulfonylurea (here iodosulfuron-methyl-sodium) is observed after storage at 35° C. for 3 to 4 months. In contrast, under the same storage conditions, a degradation of from 10 to 15% is observed when the emulsifier used is a surfactant which is not blocked terminally, such as ®Genapol X-060 (Example 4) or ®Genapol O-050 (Example 10). However, when stored at ambient temperature (from 20 to 25° C.), even the latter formulations are storage-stable. Thus, formulations of type 4 or 12 still have the full content of active compound even when stored for 18 months in this temperature range.

The proportion of emulsifier (component d) is, for example, in the range from 0.5 to 40% by weight, preferably from 0.5 to 20% by weight, in particular from 5 to 15% by weight, based on the weight of the formulation.

To improve the emulsifier properties, it is possible to add an additional ionic, preferably oil-soluble ionic, surfactant. Suitable ionic surfactants are, for example:

salts of alkylarylsulfonic acids having a linear or branched alkyl chain, partial phosphoric esters or partial sulfuric esters of in each case ethoxylated di- and tristyrylphenols, in each case as free acid or salts, for example alkali metal salts, having a degree of ethoxylation of from 6 to 16; for example phosphated ethoxylated tristyrylphenols, for example those having from 5 to 20 EO, preferably 16 EO (®Soprophor FL, Rhodia)

phosphated ethoxylated alkylphenols (partial esters) or salts thereof, for example ®Soprophor PA 17, 19, 21 or 23 or MB or the potassium salts ®Soprophor PS 17, 19, 21 or 23;

sulfated ethoxylated distyrylphenols having preferably 5 to 15 EO, for example ®Soprophor DSS 4, 5, 7 or 15;

sulfated ethoxylated tristyrylphenols having preferably 5 to 20 EO, in particular 16 EO, for example ®Soprophor 4 D 384.

Preference is given to alkali metal salts and alkaline earth metal salts of alkylbenzenesulfonic acids, in particular calcium dodecylbenzenesulfonate (®Phenylsulfonat CA, ®Phenylsulfonat CAL (both from Clariant) or ®Emcol P 18.60, ®Emcol P 58.60 (both from Witco)).

The proportion of ionic emulsifier (component e) is, for example, in the range of from 0 to 20% by weight, preferably from 0 to 10% by weight, in particular from 0.1 to 10% by weight, based on the weight of the formulation.

The weight ratio of components a)+b) to components d)+e) is preferably in the range from 10:1 to 1:100, in particular from 2:1 to 1:50, very particularly from 1:1 to 1:5.

To control the sedimentation behavior of the dispersed sulfonylurea, the formulations preferably comprise thickeners and/or thixotropic agents (component f). Suitable thickeners and/or thixotropic agents are synthetic or natural mineral products and/or organic rheological additives, in particular those which are suitable for nonaqueous formulations.

Suitable thickeners from the class of the mineral thickeners are pure silica, for example of the type ®Sipernat, ®Wessalon or ®Aerosil from Degussa, or mixed oxides, for example magnesium/aluminum silicates, such as attapulgite (®Attagel 40, Attagel 50 from Engelhard) or magnesium phyllosilicates, such as bentonites or hectorites. Particularly suitable are, for example, organically modified hectorites, such as ®Bentone 27, Bentone 34 or Bentone 38, which are manufactured by Rheox.

Other organic additives suitable for controlling the rheological properties of the formulation are thickeners and/or thixotropic agents from the group of certain polyamides, such as ®Thixa SR, ®Mixatrol SR 100 or ®Mixatrol TSR, and polyesters, such as ®Thixatrol 289; all products from Rheox Products based on castor oil, such as ®Thixicia E, ®Thixain R, ®Thixatrol ST or ®Thixatrol GST, likewise from Rheox, were found to be particularly effective for preventing sedimentation of the sulfonylurea.

The formulations can be prepared without component f) and, in individual cases, they are sufficiently stable, depending on the concentration and the sedimentation tendency of the sulfonylurea. The amounts of thickener and thixotropic agent which are preferably employed depend on the respective composition of the solvent/surfactant mixture and are generally in the range from 0.1 to 10% by weight, in particular from 0.2 to 5% by weight, very particularly preferably from 0.5 to 2.0% by weight, based on the weight of the formulation.

The formulation auxiliaries mentioned, such as surfactants, solvents and other additives, are customary or known auxiliaries and are described, for example, in: Winnacker-Küchler, "Chemische Technologie" [Chemical Technology], Volume 7, C. Hauser Verlag Munich, 4th Ed. 1986; van Valkenburg, "Pesticides Formulations", Marcel Dekker N.Y., 1973; Watkins, "Handbook of Insecticide Dust Diluents and Carriers", 2nd Ed., Darland Books, Caldwell N.J.; H. v. Olphen, "Introduction to Clay Colloid Chemistry"; 2nd Ed., J. Wiley & Sons, N.Y.; Marsden, "Solvents Guide", 2nd Ed., Interscience, N.Y. 1950; McCutcheon's, "Detergents and Emulsifiers Annual", MC Publ. Corp., Ridegewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesellschaft, Stuttgart 1976. Other sources are the data sheets and company brochures of the respective manufacturers and vendors.

The formulations comprise, for example, a) from 0.1 to 50% by weight, preferably from 0.1 to 20% by weight, in particular from 0.2 to 5% by weight, of one or more sulfonylureas, b) from 0.1 to 60% by weight of one or more active compounds which are partially or completely dissolved in component c), for example from 0.5 to 50% by weight, preferably from 2 to 30% by weight, in particular from 5 to 15% by weight of one or more herbicides, for example phenoxypropionic acid derivatives, or from 0.1 to 40% by weight, preferably from 0.1 to 20% by weight, in particular from 0.1 to 5% by weight of one or more safeners or from 0.6 to 60% by weight, preferably from 3 to 50% by weight, in particular from 5.1 to 15% by weight of a mixture of from 0.5 to 50% by weight, preferably 2 to 30% by weight, in particular from 5 to 10% by weight, of a herbicide, for example a phenoxypropionic acid derivative, and from 0.1 to 40% by weight, preferably from 0.1 to 20% by weight, in particular from 0.1 to 5% by weight, of safener, c) from 5 to 95% by weight, preferably from 10 to 90% by weight, in particular from 40 to 80% by weight, of an organic solvent or solvent mixture, d) from 0.5 to 40% by weight, preferably from 0.5 to 20% by weight, in particular from 5 to 15% by weight, of one or more nonionic emulsifiers, e) from 0 to 20% by weight, preferably from 0 to 10% by weight, of one or more ionic emulsifiers, f) from 0 to 10% by weight, preferably from 0.1 to 10% by weight, in particular from 0.2 to 5% by weight, of one or more thickeners or thixotropic agents, and no water or up to 20 percent by weight, preferably no water or up to 10% by weight of water, in particular in dissolved form, where the content of components a) and b) (total content of active compound) is in the range from 0.1 to 60% by weight, preferably from 0.6 to 50% by weight, in particular from 2.5 to 25% by weight.

The weight percentages are in each case based on the weight of the total preparation.

The preparation of the suspension concentrates according to the invention, which for their part are suspensions, can be carried out by customary processes suitable for preparing suspensions. According to a standard process, all components are mixed and ground in suitable apparatus, for example using a stirred ball mill. For finely distributing the solid sulfonylurea, mean particle sizes of 50 µm or less, preferably 10 µm or less, in particular from 1 to 5 µm, are generally advantageous.

Using the non-aqueous or low-water suspension concentrates according to the invention, it is possible to produce a liquid stable preparation of sulfonylureas having favorable use properties. According to the invention, it is also possible to produce stable preparations for the joint formulation of herbicidal sulfonylureas and safeners or sulfonylureas with herbicides, for example from the group of the phenoxypropionic acid derivatives, in addition to suitable safeners.

In particular cases, the stability of the formulations is excellent, even under thermal stress. In addition, many of the formulations have favorable use properties. During application of the suspension concentrates, where they are usually initially diluted with water to the use concentration giving sprayable suspensions which are then applied, similar or even improved herbicidal effects are achieved, compared to the WP formulations or the WG formulations. Similarly, in the case of mixed formulations with safeners or herbicides such as phenoxypropionates, if appropriate in the presence of safeners, equally good or often even increased or longer lasting herbicidal action, with the same selectivity in crops, is observed compared to tank mixes of separate formulations of the sulonlyureas, safeners or phenoxypropionates and optionally safeners.

Accordingly, the invention also provides the use of a preparation according to the invention as crop protection composition for controlling harmful plants.

This can be effected by diluting an effective amount of the herbicidal preparation to the use concentration, giving an aqueous suspension, and applying the aqueous suspension to the harmful plants, parts of plants, plant seeds, to the area on which the plants grow or are to be controlled, or to an area of useful plants under cultivation, which are to be protected against harmful plants.

The tables below list some formulations which are stable on storage for more than 3 months at 35° C. and which, in particular, show no degradation or only slight degradation (less than 5%) of the active compounds (herbicide/safener). The suspension concentrates were prepared by mixing and grinding the components in a stirred ball mill.

In Tables 1 and 2 below, the amounts, including percentages, are based on eight, unless defined otherwise.

Abbreviations for Tables 1 and 2:

iodosulfuron=3-(4-methoxy-6-methyl-1,3,5-triazin-2-yl)-1-(2-carboxy-5-iodophenylsulfonyl)urea iodosulfuron-methyl-sodium=3-(4-methoxy-6-methyl-1,3,5-triazin-2-yl)-1-(2-methoxycarbonyl-5-iodophenylsulfonyl)urea, sodium salt, fenoxaprop-P-ethyl=ethyl (R)-2-[4-(6-chlorobenzoxazol-2-yloxy)phenoxy]propionate, sulfonylurea A1=N,N-dimethyl-2-[3-(4,6-dimethoxypyrimidin-2-yl)ureidosulfonyl]4-formylaminobenzamide, sulfonylurea A2=methyl 2-[3-(4,6-dimethoxypyrimidin-2-yl)ureidosulfonyl]4-methylsulfonylamidomethylbenzoate, mefenpyr-diethyl=ethyl 1-(2,4-dichlorophenyl)-5-(ethoxycarbonyl)-5-methyl-2-pyrazoline-3-carboxylate, isoxadifen-ethyl=ethyl 5,5-diphenyl-2-isoxazolinecarboxylate, ®Solvesso 150=mineral oil with aromatic fractions; boiling range 187–207° C.,
®Solvesso 200=mineral oil with aromatic fractions; boiling range 219–282° C.,
rapeseed oil fatty acid methyl ester=rapeseed oil derivative,
®Genapol X-060=ethoxylated isotridecyl alcohol having 6 EO (Clariant)
®Genapol X-060 methylether=Genapol X-060 which is terminally etherified with methyl,
®Genapol X-150=ethoxylated isotridecyl alcohol having 15 EO (Clariant),
®Genapol O-050=ethoxylated unsaturated ($C_{16}$–$C_{18}$)-fatty alcohol (mainly oleyl alcohol) having 5 EO (Clariant),
®Pluronic L 121, corresponds to ®Synperonic L 121=block copolymer of ethylene oxide and propylene oxide,
®Soprophor S/40-P=ethoxylated tristyrylphenol having 40 EO,
®Soprophor BSU=ethoxylated tristyrylphenol having 16 EO,
®Atplus 309 F=ethoxylated sorbitan ester,
®Emulsogen EL 400=ethoxylated fatty acid,
®Emcol P 18.60=calcium dodecylbenzenesulfonate,
®Bentone 27=organically modified hectorite (mineral thickener),
®Bentone 38=organically modified hectorite (mineral thickener),
®Thixatrol ST=thixotropic agent based on an organic castor oil derivative.

COMPARATIVE EXAMPLES

With respect to the active compounds, the formulations of Examples 1 to 12 from Table 1 are storage-stable for 3 months at 35° C. The formulations of Examples 2/1 to 2/4 are storage-stable for 4 months at 40° C. The formulations of Examples 5 and 6 are stable even at higher temperatures, for example at 54° C. for more than two weeks. In contrast, if the active compounds are formulated as suspoemulsions according to EP-A-0514769, under in each case identical storage conditions substantial decomposition of the respective active compounds from the group of the sulfonylureas is observed.

What is claimed is:

1. A preparation in the form of a liquid suspension concentrate, which comprises
  a) one or more solid herbicidally active compounds from the group of sulfonylureas in suspended form wherein the sulfonylureas are selected from the group consisting of
    A1) phenyl- and benzylsulfonylureas or salts thereof,
    A2) thienylsulfonylureas or salts thereof, and
    A4) sulfonyldiamide-derivatives or salts thereof,
    A6) alkoxyphenoxysulfonylureas or salts thereof,
  b) one or more active ingredients which are partially or completely dissolved in component c),
  c) an organic solvent or solvent mixture,
  d) one or more nonionic emulsifiers,
  e) optionally one or more ionic emulsifiers, and
  f) optionally one or more thickeners or thixotropic agents
whereby said preparation either does not contain any water or contains up to 30 percent by weight of water in dissolved form.

2. A preparation as claimed in claim 1, which comprises
  a) from 0.1 to 50% by weight of one or more sulfonylureas,
  b) from 0.1 to 60% by weight of one or more active compounds which are partially or completely dissolved in component c),
  c) from 5 to 95% by weight of an organic solvent or solvent mixture,
  d) from 0.5 to 40% by weight of one or more nonionic emulsifiers,
  e) from 0 to 20% by weight of one or more ionic emulsifiers,
  f) from 0 to 10% by weight of one or more thickeners or thixotropic agents,
and no water or up to 20 percent by weight of water in dissolved form, where the amount of components a) and b) (total amount of active compound) is in the range from 0.1 to 60% by weight.

3. A preparation as claimed in claim 1, which comprises, as component b), from 0.5 to 50% by weight of one or more substituted phenoxypropionic acid derivatives or from 0.1 to 40% by weight of one or more safeners or from 0.6 to 60% by weight of a mixture of from 0.5 to 50% by weight of phenoxypropionic acid derivative and from 0.1 to 40% by weight of safener.

4. A preparation as claimed in claim 1, which comprises
  a) from 0.1 to 20% by weight of one or more sulfonylureas,
  b) from 2 to 30% by weight of one or more phenoxypropionic acid derivatives or from 0.1 to 40% by weight of one or more safeners or from 3 to 50% by weight of a mixture of from 2 to 30% by weight of phenoxypropionic acid derivative and from 0.1 to 40% by weight of safener,
  c) from 10 to 90% by weight of organic solvent or solvent mixture,
  d) from 0.5 to 20% by weight of one or more nonionic emulsifiers,
  e) from 0 to 10% by weight of one or more ionic emulsifiers,
  f) from 0.1 to 10% by weight of one or more thickeners or thixotropic agents,
and no water or up to 10 percent by weight of water in dissolved form, where the amount of components a) and b) (total amount of active compound) is in the range from 0.6 to 50% by weight.

5. A preparation as claimed in claim 1, which comprises
  a) from 0.2 to 5% by weight of one or more sulfonylureas,
  b) from 5 to 15% by weight of one or more phenoxypropionic acid derivatives or from 0.1 to 5% by weight of one or more safeners or from 5.1 to 15% by weight of a mixture of from 5 to 10% by weight of phenoxypropionic acid derivative and from 0.1 to 5% by weight of safener,
  c) from 40 to 80% by weight of organic solvent or solvent mixture,
  d) from 5 to 15% by weight of one or more nonionic emulsifiers,
  e) from 0 to 10% by weight of one or more ionic emulsifiers,
  f) from 0.2 to 5% by weight of one or more thickeners or thixotropic agents,
and no water or up to 10 percent by weight of water in dissolved form, where the amount of components a) and b) (total amount of active compound) is in the range from 2.5 to 25% by weight.

6. A preparation as claimed of claim 1, which comprises, as component a), one or more sulfonylureas selected from the group consisting of chlorsulfuron, chlorimuron-ethyl, metsulfuron-methyl, triasulfuron, cinosulfuron, prosulfuron, ethametsulfuron-methyl, sulfometuron-methyl, tribenuron-methyl, bensulfuron-methyl, primisulfuron-methyl, iodosulfuron-methyl, triflusulfuron-methyl, oxasulfuron, methyl 2-[3-(4,6-dimethoxypyrimidin-2-yl)ureidosulfonyl]-4-methylsulfonylamidomethylbenzoate, N,N-dimethyl-2-[3-(4,6-dimethoxypyrimidin-2-yl)ureidosulfonyl]-4-formylaminobenzamide, thifensulfuron-methyl, amidosulfuron, ethoxysulfuron and salts thereof, in particular chlorsulfuron, chlorimuron-ethyl, metsulfuron-methyl, triasulfuron, cinosulfuron, prosulfuron, ethametsulfuron-methyl, sulfometuron-methyl, tribenuron-methyl, bensulfuron-methyl, primisulfuron-methyl, iodosulfuron-methyl-sodium, triflusulfuron-methyl, methyl 2-[3-(4,6-dimethoxypyrimidin-2-yl)ureidosulfonyl]-4-methylsulfonylamidomethylbenzoate, N,N-dimethyl-2-[3-(4,6-dimethoxypyrimidin-2-yl)ureidosulfonyl]-4-formylaminobenzamide, thifensulfuron-methyl, amidosulfuron, ethoxysulfuron and salts thereof.

7. A preparation as claimed in claim 1, which comprises, as component b), one or more herbicides selected from the group consisting of diclofop-methyl, cyhalofop-butyl, pirifenop-butyl, haloxyfop-methyl, haloxyfop-P-methyl, clodinafop-propargyl, fluazifop-butyl, fluazifop-P-butyl, quizalofop-methyl or -ethyl or -tefuryl, quizalofop-P-methyl or -ethyl or -tefuryl, propaquizafop, fenoxaprop-ethyl, fenoxaprop-P-ethyl and optionally a safener.

8. A preparation as claimed in claim 1, which comprises, as component c)
   1. a nonpolar solvent selected from the group consisting of
      aromatic solvents which are derived from benzene,
      aliphatic hydrocarbons and
      mixtures of aromatic and aliphatic hydrocarbons or
   2. a polar lipophilic solvent selected from the group consisting of
      oils,
      esters selected from the group of the aliphatic carboxylic esters,
      esters of aromatic carboxylic acids,
      esters of other organic acids and
      mixtures of the solvents mentioned or
   3. mixtures of solvents from 1. and 2.

9. A preparation as claimed in claim 1, which comprises, as component d), an emulsifier or an emulsifier mixture selected from the group consisting of
   ethoxylated, saturated and unsaturated aliphatic alcohols,
   terminally etherified ethoxylated, saturated and unsaturated aliphatic alcohols,
   ethoxylated arylalkylphenols,
   ethoxylated alkylphenols having one or more alkyl radicals,
   ethoxylated hydroxyfatty acids,
   surfactants from the group of the ethoxylated sorbitan esters,
   block copolymers of ethylene oxide and propylene oxide,
   condensates of EO-PO block copolymers and ethylenediamine and
   mixtures of the nonionic surfactants mentioned.

10. A preparation as claimed in claim 1, which comprises, as component f), a thickener or thixotropic agent selected from the group consisting of synthetic mineral products, natural mineral products and organic additives.

11. A process for preparing a composition as claimed in claim 1, which comprises mixing and, if appropriate, grinding the components of the preparation.

12. A method for controlling harmful plants in crops of useful plants, which comprises applying a herbicidal preparation as claimed in claim 1 as crop protection composition.

13. A method as claimed in claim 12, which comprises diluting an effective amount of the herbicidal preparation to the use concentration, giving an aqueous suspension, and applying the aqueous suspension to the harmful plants, parts of plants, plant seeds, to the area on which the plants grow or are to be controlled, or to an area of useful plants under cultivation, which are to be protected against harmful plants.

14. A preparation in the form of a liquid suspension in concentrate which comprises
   a) one or more solid herbicidally active compounds from the group of sulfonylureas in suspended form wherein the sulfonylureas are selected from the group consisting of
      A1) phenyl- and benzylsulfonylureas or salts thereof,
      A2) thienylsulfonylureas or salts thereof, and
      A4) sulfonyldiamide-derivatives or salts thereof,
      A6) alkoxyphenoxysulfonylureas or salts thereof
   b) one or more non-sulfonylurea compounds, which are partly or completely dissolve in component c), said compounds being a compound selected from the group consisting of phenoxypropionic acid derivatives, monocyclic heteraryloxyphenoxyalkanecarboxylic acid derivatives, bicyclic heteroaryloxyphenoxyalkanecarboxylic acid derivative, and safeners;
   c) an organic solvent or an organic solvent mixture, wherein said solvent or solvent mixture is selected from a class of solvents selected from the group consisting of substantially nonpolar solvents and polar lipophilic solvents;
   d) one or more nonionic emulsifiers;
   e) optionally one or more ionic emulsifiers,
   f) optionally one or more thickeners or thixotropic agent
whereby said preparation whereby said preparation either does not contain any water or contains up to 30 percent by weight of water in dissolved form.

15. The preparation according to claim 14 wherein
   the one or more non-sulfonylurea compounds is clodinefop-propargly, phenoxaprop-P-ethyl, mefenpyr-diethyl, isoxadifen-ethyl, or cloquintocet-mexyl,
   the solvent is a mineral at oil with aromatic fractions or rapeseed oil fatty acid ($C_1$–$C_4$)-alkyl esters,
   the non-ionic surfactant is an ethoxylated fatty alcohol or ester thereof having a degree of ethoxylation of from 1 to 100 EO or block copolymers of EO and PO,
   the ionic surfactant is a partial phosphoric ester or sulforic ester of ethoxylated di- and tristyrylphenols,
   the thickener is a magnesium phyllosilicate or a thixotropic agent based upon an organic castor oil derivative.

16. The preparation according to claim 14, wherein the sulfonylurea compound is iodosulfuron or iodosulfuron-methyl sodium.

* * * * *

UNITED STATES PATENT AND TRADEMARK OFFICE
CERTIFICATE OF CORRECTION

PATENT NO. : 6,479,432 B1
DATED : November 12, 2002
INVENTOR(S) : Frank Sixl

It is certified that error appears in the above-identified patent and that said Letters Patent is hereby corrected as shown below:

Column 17,
At the end of line 30, after the word "derivative", please insert Tables 1 and 2 as shown on attached pages.

Signed and Sealed this

Twenty-fourth Day of June, 2003

JAMES E. ROGAN
*Director of the United States Patent and Trademark Office*

Table 1: Examples of suspension concentrates

| Example No. | 1 | 2 | 3 | 4 | 5 | 6 | 7 | 8 | 9 | 10 | 11 | 12 |
|---|---|---|---|---|---|---|---|---|---|---|---|---|
| iodosulfuron | | | | | | | | | 1.1 | 1.1 | 1.1 | |
| iodosulfuron-methyl-sodium | 3.8 | 1.9 | 1.0 | 1.0 | 1.1 | 1.1 | 0.8 | 0.8 | | | | 1.3 |
| fenoxaprop-P-ethyl | 22.9 | 11.5 | 7.8 | 7.8 | 6.4 | 6.6 | 6.2 | 6.2 | 6.5 | 6.5 | 6.5 | 7.8 |
| mefenpyr-diethyl | 11.4 | 5.8 | 3.9 | 3.9 | 3.2 | 3.3 | 2.3 | 2.3 | 3.2 | 3.2 | 3.2 | 3.9 |
| Solvesso 150 | 40.7 | | | | | | | | | | | |
| Solvesso 200 | | 63.0 | 71.8 | 73.5 | | | 77.9 | 76.9 | | | | 83.0 |
| rapeseed oil fatty acid methyl ester | | | | | 72.3 | 71.2 | | | 71.2 | 75.4 | 71.4 | |
| Pluronic L 121 | | | 12.0 | | | | | | | | | |
| Genapol X-060 | 10.0 | 12.0 | 1.0 | | | 12.0 | | | | | 12.0 | 1.0 |
| Genapol X-060-methyl ether | | | | | | | 10.0 | 10.0 | | | | |
| Genapol O-050 | | | | | | | | | | 12.0 | | |
| Soprophor S/40-P | 8.0 | | | | | | | | | | | |
| Soprophor BSU | | | | 12.0 | | | | | | | | |
| Emcol P 18.60 | | 4.0 | 1.0 | | 4.0 | 2.0 | 2.0 | | 4.0 | | 4.0 | 1.0 |
| Bentone 27 | 3.2 | | | | | | | | | | | |
| Bentone 38 | | 1.8 | 1.5 | 1.8 | 2.0 | 1.8 | | | 2.0 | 1.8 | 1.8 | 2.0 |
| Thixatrol ST | | | | | | | 0.8 | 0.8 | | | | |
| Atplus 309 F | | | | 15.0 | | | | | 12.0 | | | |
| Emulsogen EL 400 | | | | | | | | 1.0 | | | | |

Table 2: Examples of suspension concentrates

| Example No. | 2/1 | 2/2 | 2/3 | 2/4 | 2/5 | 2/6 |
|---|---|---|---|---|---|---|
| sulfonylurea A1 | 2.3 | 2.3 | 4.7 | 4.7 | | |
| isoxadifen-ethyl | 2.3 | 2.3 | 4.7 | 4.7 | | |
| sulfonylurea A2 | | | | | 2.9 | 2.9 |
| mefenpyr-diethyl | | | | | 8.7 | 8.7 |
| Solvesso 200 | 33.3 | 33.3 | 28.4 | 33.8 | 69.9 | 70.4 |
| rapeseed oil fatty acid methyl ester | 44.1 | 44.1 | 35.4 | 38.8 | | |
| Genapol X-060 | 12.0 | | 20.8 | 12.0 | 12.0 | |
| Genapol X-150 | | | | | | 12.0 |
| Emcol P 18.60 | 4.0 | 4.0 | 4.0 | 4.0 | 4.0 | 4.0 |
| Bentone 38 | 2.0 | 2.0 | 2.0 | 2.0 | 2.5 | 2.0 |
| Atplus 309 F | | 12.0 | | | | |